(12) United States Patent
Lichtenberg (10) Patent No.: US 7,141,040 B2
(45) Date of Patent: Nov. 28, 2006

(54) SAFETY INTRAVENOUS STARTER

(76) Inventor: Edward Lichtenberg, 2401 Pennsylvania Ave., Apt. 18B27, Philadelphia, PA (US) 19130

( * ) Notice: Subject to any disclaimer, the term of this patent is extended or adjusted under 35 U.S.C. 154(b) by 0 days.

(21) Appl. No.: 11/179,955

(22) Filed: Jul. 12, 2005

(65) Prior Publication Data

US 2006/0106348 A1 May 18, 2006

Related U.S. Application Data

(60) Provisional application No. 60/629,145, filed on Nov. 18, 2004.

(51) Int. Cl.
*A61M 5/178* (2006.01)
(52) U.S. Cl. .................................. 604/164.01
(58) Field of Classification Search ........... 604/164.01, 604/110, 158, 164.08, 165.01, 165.03, 2
See application file for complete search history.

(56) References Cited

U.S. PATENT DOCUMENTS 5,376,071 A * 12/1994 Henderson .................. 604/115

2003/0032922 A1 * 2/2003 Moorehead .................. 604/110

* cited by examiner

*Primary Examiner*—Nicholas Lucchesi
*Assistant Examiner*—Laura A. Bouchelle
(74) *Attorney, Agent, or Firm*—Synnestvedt & Lechner LLP

(57) ABSTRACT

An intravenous starter device having means for safely disposing of the needle. The intravenous starter device has a first tube having a first end for insertion into a patient and an outer tube in fluid communication with the first tube and having an opening for receiving fluids to be delivered to the patient through the first tube. A receiver is connected to and in fluid communication with the outer tube, and has an opening for receiving fluids. The needle is positioned within the first tube and extends therefrom for insertion into the patient. After use of the needle, a pull member connected to the needle by a pull wire is operated to pull the needle into an inner tube positioned within the outer tube whereby the needle, safely within the inner tube, can be safely removed and disposed, leaving the first tube in the patient for the catheter.

20 Claims, 5 Drawing Sheets

SAFETY INTRAVENOUS STARTER

CROSS-REFERENCE TO RELATED APPLICATIONS

The present patent application claims the benefit of U.S. Provisional Application Ser. No. 60/629,145 filed on Nov. 18, 2004. The content of the aforementioned application is fully incorporated by reference herein.

TECHNICAL FIELD

This invention relates generally to needle-bearing medical devices, and more particularly to a device for inserting a hollow needle into a patient's body, such as an intravenous starter for subsequent medication to the patient. More specifically, the invention relates to such a device having means for safely covering the needle after use to prevent accidental sticks.

BACKGROUND

Handling disposable medical devices with sharp piercing needles can be extremely risky for healthcare workers, providers, and patients. For example, any accidental needle puncture of the skin can expose a person, e.g. a healthcare worker, to pathogens such as hepatitis, HIV, or other infectious diseases, while exposing the employer, e.g., the hospital, to liability and treatment costs. It is imperative that steps be taken in the design of equipment for starting an intravenous line to eliminate the risk of an accidental stick. Accordingly, providing safe and convenient handling of such devices to reduce the risk of accidental needle sticks is a goal of manufacturers of needle devices.

One type of safety needle for starting an intravenous line is presently in use. After venous puncture the needle is withdrawn from the vein, leaving a capillary tube in the vein. The needle is captured in two interlocked plastic housings and is completely covered. The technician controls this action by pulling on a third tube which is attached to the needle by a plastic flexible filament. The technician, after disposing of the captured needle and tubes in a wall mounted sharps container, finally secures the capillary tube left in the vein. Medication for the patient flows through this tube.

The parts of this prior art device are bulky and, when discarded into a sharps container, reduce the quantity of the used needles which the container can hold when compared to a design having less bulky parts. This prior art device, therefore, increases the cost per needle of the sharps container and of the subsequent handling and destruction of the sharps container. Accordingly, a device that takes up less space in the sharps container is believed desirable. Furthermore, removal and disposal of the used needle occurs at a critical time—before securing the capillary tube in the patient's vein. Thus the goals of the present invention include the use of smaller and lower-cost parts, lowering the costs to the user, and enabling technician attention to secure the venous capillary prior to disposal of the protected needle.

SUMMARY OF THE INVENTION

The present invention provides an intravenous starter device having a first tube that has a first end for insertion into a patient, and a second end opposite the first end. An outer tube is in fluid communication with the first tube and has an opening for receiving fluids, such as from an intravenous bag or from medication, to be delivered to the patient through the first tube and ultimately to the patient. Connected to and in fluid communication with the outer tube is a receiver having an opening for receiving fluids to be delivered through the outer tube to the patient. A needle member is positioned within the first tube, which needle member includes a needle having a sharp end extending from the first tube for insertion into the patient's vein and a second end opposite the sharp end. A cover member is adjacent to and detachable from the receiver and positioned to close the receiver opening. Adjacent to the cover member is a pull member. An inner tube is connected to the cover member for movement therewith and is positioned within the outer tube. The inner tube is sized to be slidable within the outer tube and has a needle holding section sized to receive at least a portion of the needle within. To remove the needle, a pull wire connects the needle member to the pull member such that the needle member is moveable via pulling the pull member from a first position wherein the sharp end of the needle extends from the first tube to a second position wherein the sharp end of the needle is positioned within the inner tube.

In a preferred embodiment, the needle member includes a connector attached to the needle, and the pull wire is connected to the needle via the connector. The cover member includes an elastomeric bushing having a recess sized to receive and frictionally hold the connector when the needle member is moved to the second position.

BRIEF DESCRIPTION OF THE DRAWINGS

The following detailed description will be better understood when read in conjunction with the figures appended hereto. For the purpose of illustrating the invention, there is shown in the drawings a presently preferred embodiment. It also is understood, however, that this invention is not limited to this embodiment shown. It should be noted that the figures are not necessarily drawn to scale.

DETAILED DESCRIPTION

The present invention provides a novel safety intravenous starter. Described below is an illustrative embodiment of the present invention. The invention, however, is not limited to this example, and is to be limited only by the claims appended hereto.

Figure 1:
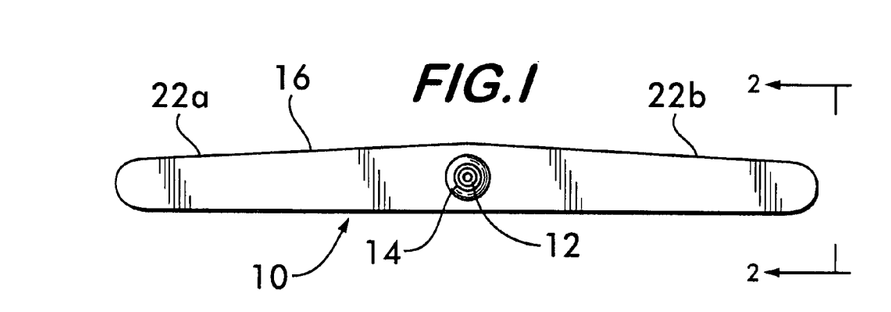
FIG. 1 shows a front end view of a device made in accordance with the present invention.
Figure 2:
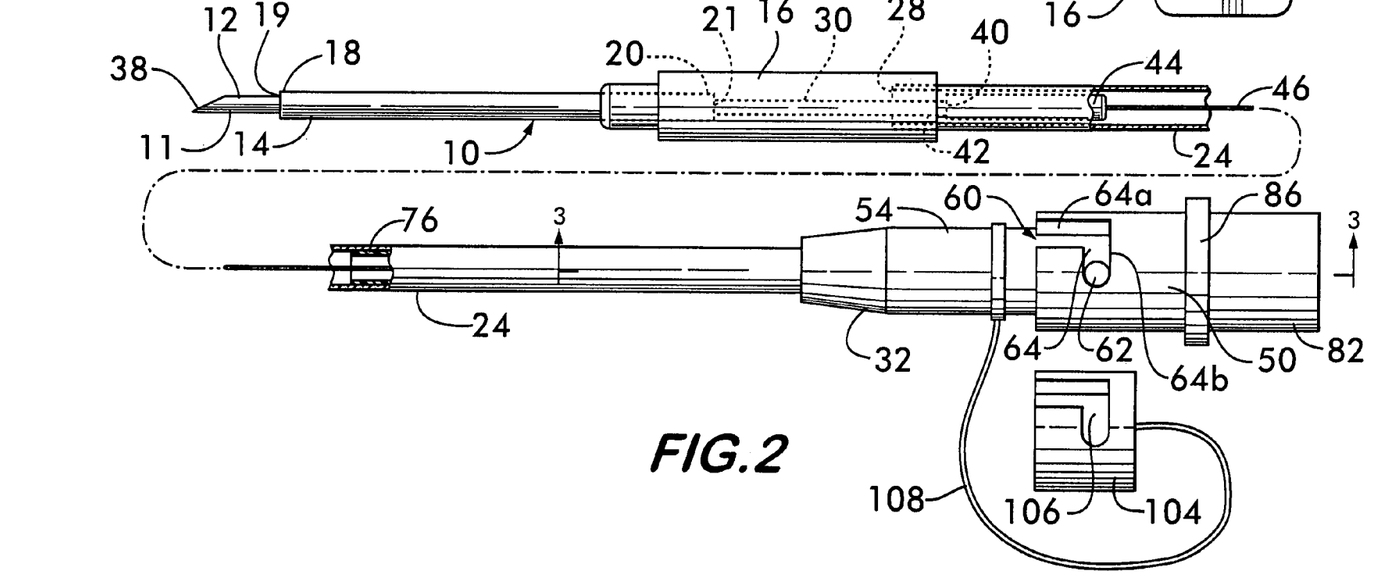
FIG. 2 shows a cross-sectional view taken along line 2—2 of the front section of the device shown in FIG. 1, and a side view of the rear section.
Figure 7:
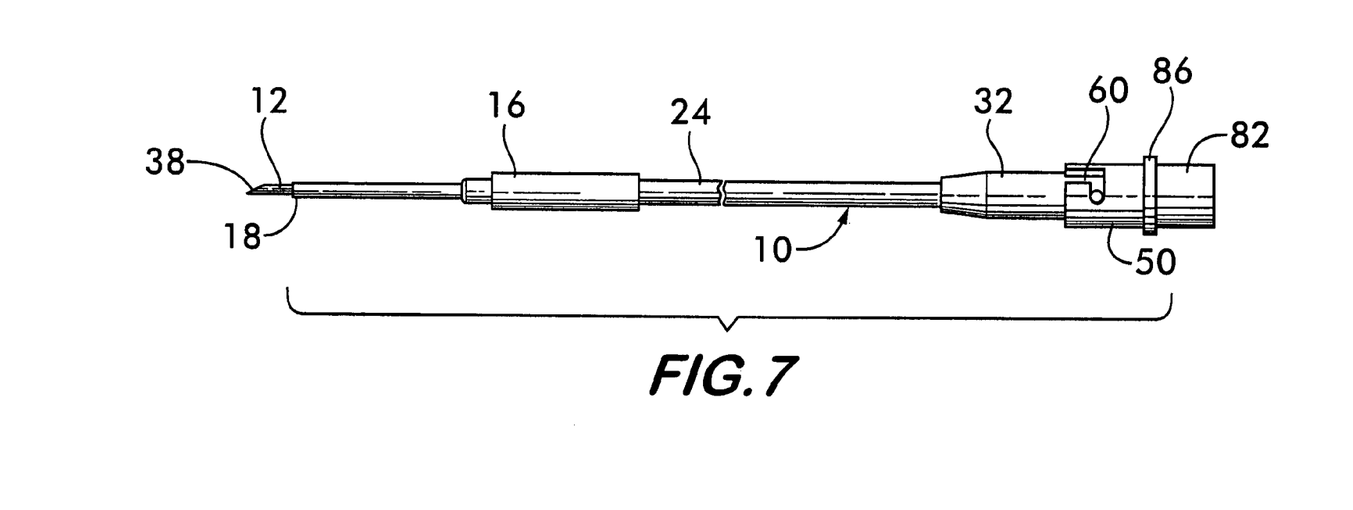
FIG. 7 is a side view of the device of FIG. 1 shown prior to use.

A safety intravenous starter device 10 of the present invention is now described with initial reference to FIGS. 1, 2 and 7. FIG. 1 shows a front end view of the device 10, FIG. 2 a side view with the left section in cross-section, and FIG. 7 shows a side view of the device 10. The intravenous starter device 10 is used to place a catheter into a vein of a patient (not shown) through which medication or other desired fluids can be administered to the patient. An elongated hollow cylindrical needle 12 is directed by the technician to puncture the vein of the patient so as to insert a first tube 14, here a cylindrical venous capillary tube or cannula, into the vein. A holder 16, such as the butterfly shaped holder illustrated, allows secure placement of the needle 12 by the technician. Once the first tube 14 is inserted into the vein, blood flows through the first tube 14 and the needle 12. The needle 12 is then withdrawn, leaving the first tube 14 in the vein so that intravenous fluids can be administered to the patient in a process described in more detail below. A more detailed description of the device 10 will now be provided, followed by a more detailed description of the use of the device 10.

Figure 1A:
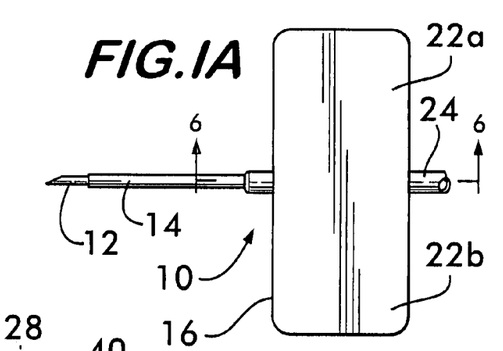
FIG. 1A shows a top view of the holder section of the device shown in FIG. 1.
Figure 3:
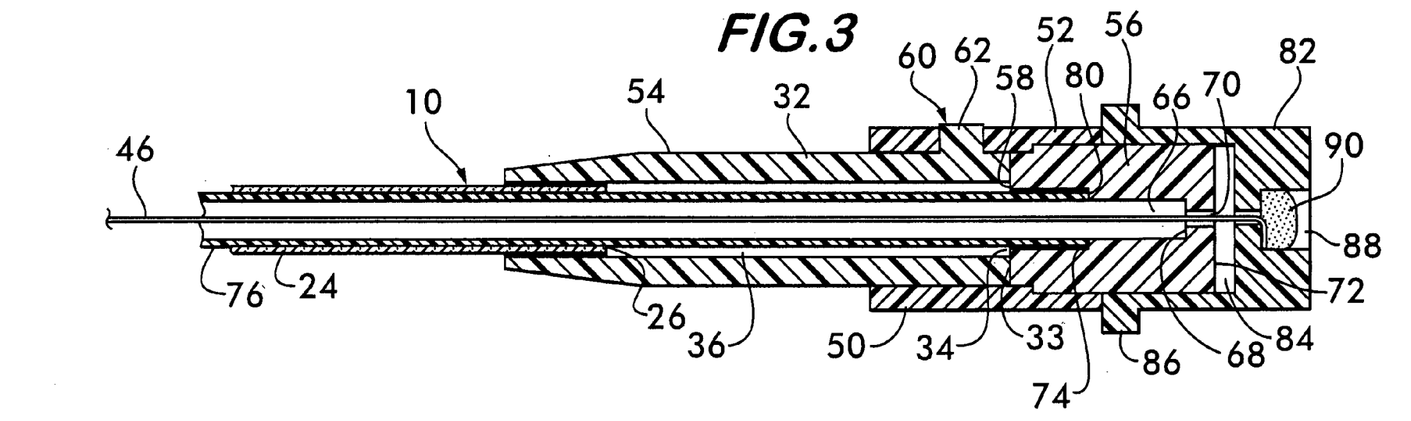
FIG. 3 shows an enlarged sectional view taken along line 3—3 of FIG. 2.

With reference to FIGS. 2, 3 and 7, the safety intravenous starter device 10 includes the first tube 14, here the venous capillary tube or cannula, which can be made of any suitable material as known in the art, such as a medical quality plastic. The first tube 14 has a first end 18 having an opening 19 which is placed into the patient's vein and through which the intravenous fluid flows from the device 10 into the patient. The first tube 14 also has a second end 20 having an opening 21 opposite the first end. Connected to the first tube 14 at the second end 20 is the holder 16 which is hand grippable so as to enable the user of the device 10 to manipulate the device 10 during use. The holder 16 is preferably in the form of a butterfly shape as shown in FIGS. 1 and 1A, having opposing arms 22a and 22b extending in opposite directions.

A cylindrical outer tube 24 is in fluid communication with the opening 21 in the end 20 of the first tube 14 such that fluids can flow from the outer tube 24 to the first tube 14. As seen, the outer tube 24 has an inlet opening 26 (FIG. 3) for receiving fluids and an outlet opening 28 (FIG. 2) through which fluids exit the outer tube 24 into the first tube 14, flowing towards the patient. As seen in the present embodiment, the first tube 14 and the outer tube 24 are connected to one another via the holder 16 to which both tubes 14 and 24 are attached, preferably with an adhesive or any other suitable connection means. Here the two tubes 14 and 24 do not physically contact one another, but fluidly communicate through a longitudinal channel 30 (FIG. 2) formed in the holder 16 to which the tube 14 is fixedly attached as shown, and through which the fluid flows from the outer tube 24 to the first tube 14 when delivering fluids to the patient.

A receiver 32 (FIGS. 2 and 3) is connected to an end of the outer tube 24 so as to be in fluid communication therewith. The receiver 32 has a rear end 33 having an opening 34 for receiving fluids from a supply of fluids to be delivered to the patient, e.g., the supply line from an intravenous bag or from a medication vial. With particular reference to FIG. 3, in the present embodiment, it is seen that the receiver 32 has an internal longitudinal cylindrical fluid conduit 36 fluidly connecting the receiver opening 34 to the opening 26 of the outer tube 24 which is securely attached to the receiver 32 as shown, such as by an adhesive.

Figure 5:
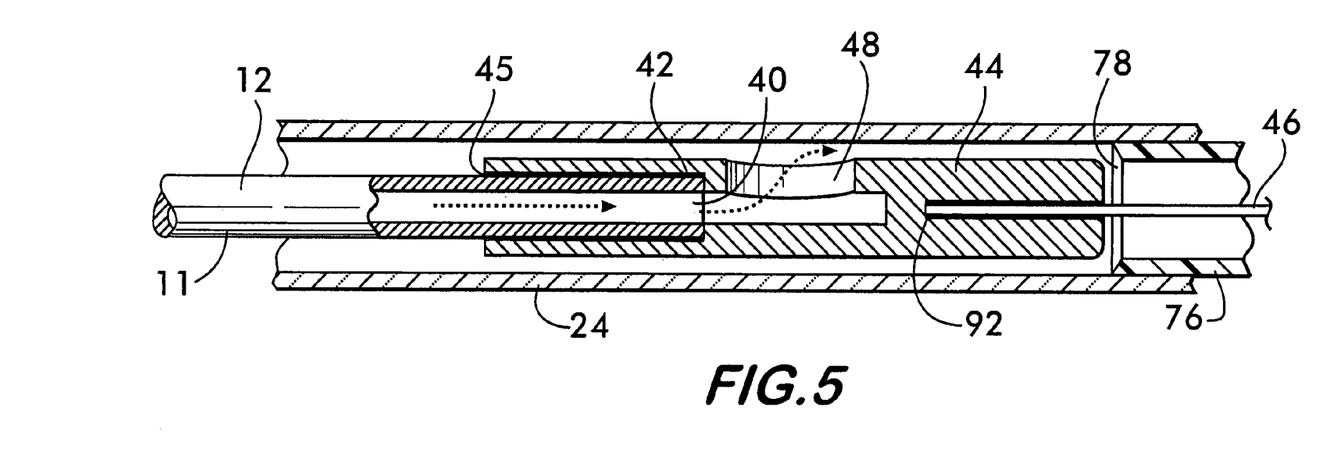
FIG. 5 shows an enlarged cross-sectional view of the connector and needle entering the inner tube.

With reference to FIGS. 2 and 7, a needle member 11 is positioned slideably within the first tube 14. The needle member 11 includes the needle 12 which has a sharp end 38 extending beyond the end 18 of the first tube 14 as shown for guiding the first tube end 18 into the patient's vein as known in the art. The needle 12 further has an opening 40 at a second end 42 opposite the sharp end 38 (FIG. 5). In the preferred embodiment, the needle member 11 also includes a connector 44 which holds the needle 12 within a channel 45, and which is used to connect the needle 12 to a pull wire 46 as further described below. The connector 44 has an opening 48 in fluid communication with the needle opening 40 so that blood from the patient can flow through the needle 12 and out the opening 48 into the outer tube 24, which is preferably made of a translucent material, to indicate that the vein was successfully punctured. Although it fits within the first tube 14, the needle member 11 is slideably displaceable relative to the tube 14 so as to be capable of being withdrawn therefrom after the tube 14 has been inserted into the vein as is known in the art.

Figure 3A:
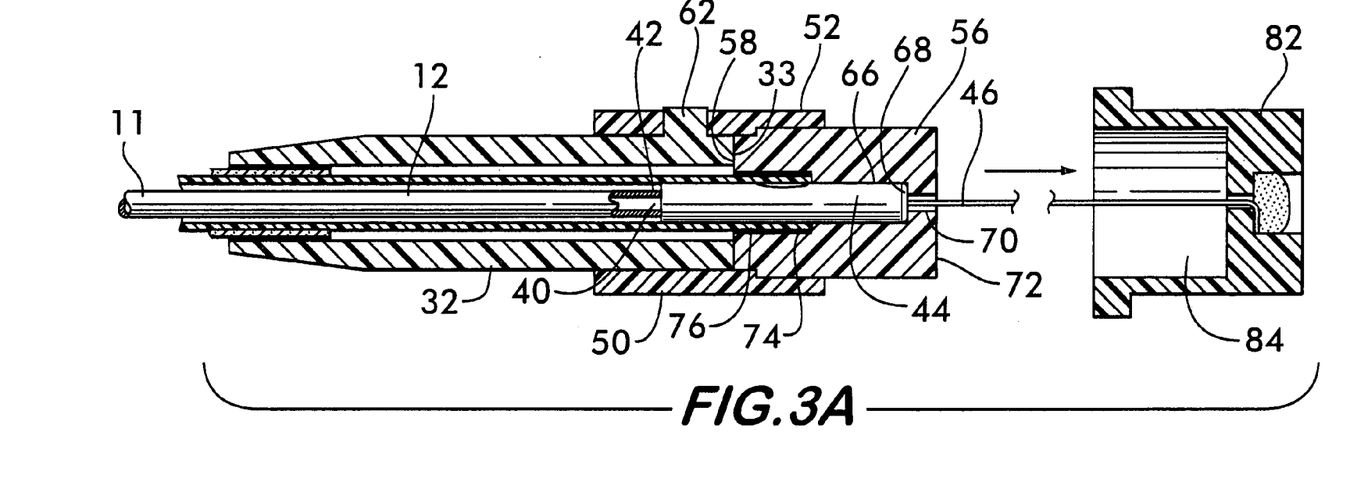
FIG. 3A shows a cross-sectional view of the rear section of FIG. 3 with the needle member in the safety position.

At the opposite end of the device 10 from the needle 12 is a cover member 50 detachably connected to the receiver 32 for closing the receiver opening 34. As seen in FIGS. 3 and 3A, the cover member 50 includes a hollowed body 52 configured to fit over the outer surface 54 of the receiver 32 as shown, and further has an elastomeric bushing 56 fixedly attached within the rear section of and extending rearward from the body 52 as shown. A front end 58 of the bushing 56 is in compressive contact against the rear end 33 of the receiver 32 to effect a seal as shown. This compressive seal of the cover member bushing 56 and the receiver 32 can be broken and the two parts separated through the action of a bayonet type lock 60. This lock 60 includes a cylindrical projection or knob 62 attached to and extending from the outer surface 54 of the receiver member 32 and which is displaceable within a complimentary L shaped slot 64 having a longitudinal section 64a and a transverse section 64b formed in the cover member body 52. As the knob 62 moves into the longitudinal slot section 64a, the bushing 56 contacts the receiver end 33. Rotation of the knob 62 into the transverse slot section 64b provides a camming action which further compresses the bushing 56 against the receiver 32. One way of accomplishing this is to provide a tolerance of about 0.002 inches additional distance that the receiver 32 and cover member 50 travel relative to one another after initial contact. For example, movement of the knob 62 into the longitudinal slot section 64a up to the transverse slot section 64b brings the cover member bushing end 58 and the receiver end 33 into contact. The transverse slot 64b is positioned to provide the 0.002 inch further movement such that rotation of the knob 62 into the transverse slot 64b causes the bushing and receiver to compress relative to one another. Reversal of the knob rotation motion allows the receiver and cover member 32 and 50 to be separated during the disposal process as described below. The cover member elastomeric bushing 56 has a recess 66 sized to receive and frictionally hold the needle member 11; in the preferred embodiment illustrated the connector 44 of the needle member 11 is frictionally held in the bushing recess 66 as shown in FIG. 3A. The end of the recess 66 has a stop 68 for stopping the movement of the needle member 11 within the recess 66. The bushing 56 further has a smaller diameter opening 70 extending from the recess 66 to the back end 72 of the bushing (FIG. 3). At its front end, the recess 66 opens to a larger diameter recess 74 in which is fixedly attached an inner tube 76 as further described below.

Figure 10:
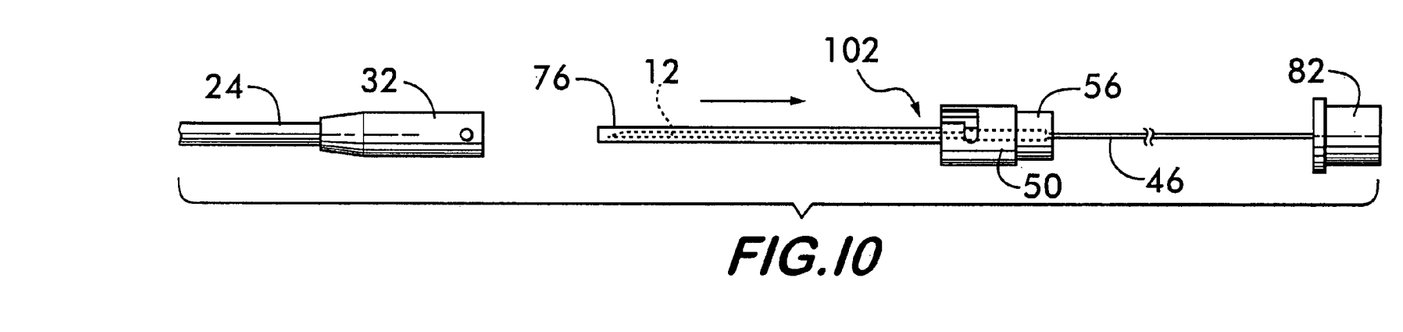
FIG. 10 is a side view of the needle assembly of the device with the needle in its safety position after removal from the device of FIG. 9.

Attached to and extending from the bushing 56 of the cover member 50 towards the needle member 11, positioned within the outer tube 24, is the cylindrical inner tube 76. The needle member 11, including the needle 12, is slidable into and within the inner tube 76 from a first position where the needle 12 is positioned for insertion into a patient as shown in FIG. 2 (the sharp end 38 extending out of the tube 14) to a second or final position where the sharp end 38 of the needle 12 is within the inner tube 76 and the needle member 11 is held in place within the bushing recess 66 by friction as described in more detail below (FIGS. 3A and 10). This second position can also be referred to as the safety position. In the present embodiment, the inner tube 76 has one end having an opening 78 (FIG. 5) for receiving the needle member 11 and a second end 80 (FIG. 3) fixedly attached or joined to the cover member within the recess 74 of the cover member bushing 56 so that the inner tube 76 is moveable with the cover member 50. The inner tube 76 is preferably made of a flexible plastic material and is sized to have sufficient clearance within the outer tube 24 and the receiver member 32 so that the inner tube 76 can be slidably withdrawn from the outer tube 24 for removal of the needle as further described below.

With reference to FIGS. 2, 3 and 7, a pull member 82 adjacent to the cover member 50 as shown is detachably connected to the bushing 56 of the cover member 50 so as to be moveable to the right as oriented in FIGS. 2 and 3 relative to the cover member 50. In the illustrated embodiment, the pull member 82 has a recess 84 that snugly and detachably fits onto a portion of the outer surface of the bushing 56 that extends out of the rear side of the cover member 50 (see FIG. 3A showing the bushing 56 with the pull member 82 removed). A ring like projection 86 extending from the pull member 82 can be provided for ease of removing the pull member.

Figure 4:
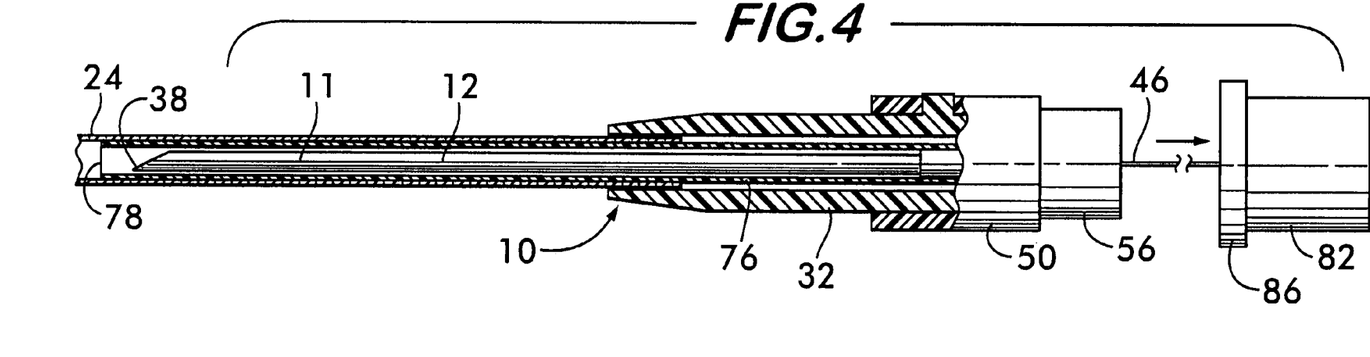
FIG. 4 is a sectional view of the rear end of the device as shown in FIG. 2 with the needle member in the safety position.

Extending from the pull member 82 to the needle member 11 through the inner tube 76 is the pull wire 46 for pulling the needle 12 from its initial or first position where the needle can puncture the patient's vein as shown in FIG. 2, to the second position wherein the sharp end of the needle 12 is covered within the inner tube 76 as shown in FIG. 4. The pull wire 46 extends through the bushing opening 70 with sufficient clearance such that the pull wire 46 can move therethough. The pull wire 46 is preferably formed of a flexible filament and attached to the pull member 82 in a recess 88 with an adhesive 90. With further reference to FIG. 5, the opposite end 92 of the pull wire 46 is preferably attached to the needle member 11 via the connector 44 (FIGS. 2, 5), adhered at one end to the needle 12 and at its other end to the pull wire 46. Sufficient clearance is provided between the connector 44, and the inner diameter of the inner tube 76 so that the needle member 11 can be slidably moved through the inner tube 76 towards the bushing 56 until the connector hits the stop 68 in the bushing recess as seen in FIG. 3A.

Figure 6:
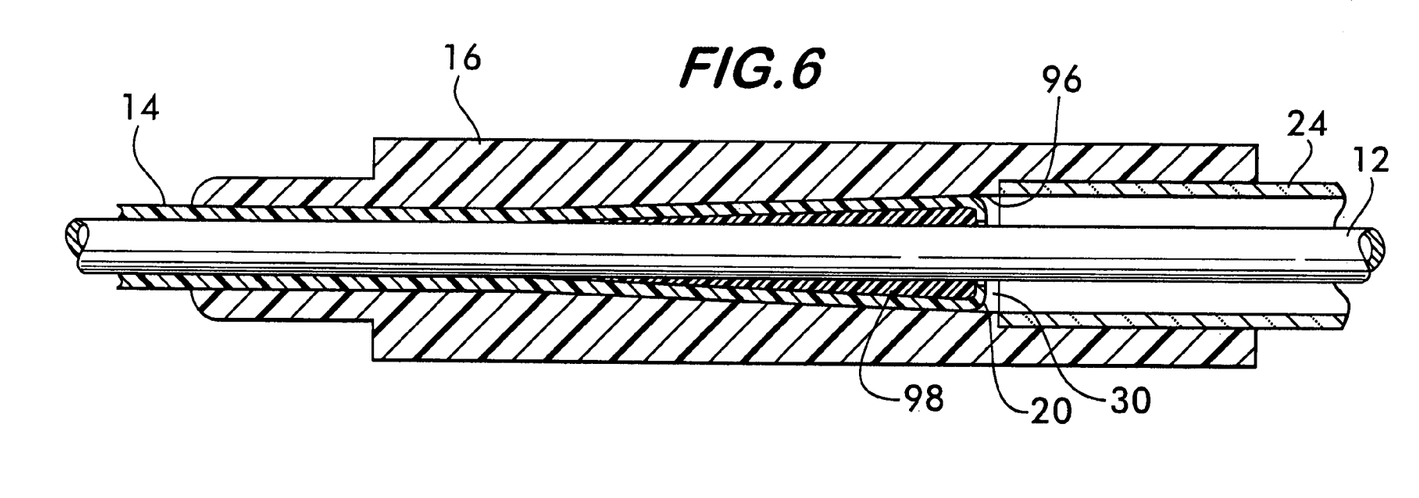
FIG. 6 is an enlarged cross sectional view of the holder showing preferred connection method of the first tube to the holder.

With reference to FIG. 6, a preferred configuration for securing the first tube 14 to the holder 16 is illustrated. Since the first tube 14 of the present embodiment is of such a small diameter (about 0.04 inches), it may not be reliably glued to the holder 16. Furthermore, if it were glued and became loose under continued use, it might float freely and enter the vein, which could be life threatening. A novel design preferred in the present embodiment prevents this problem. Here, the holder channel 30 has a tapered section 96 that is angled as shown. About a 6 degree included angle is believed preferable. A wedge 98 having a matching angle, here about 6 degrees, wedges the first tube end 20 against the tapered section 96 to lock the first tube 14 to the holder 16. The needle 12 is shown slidably fitting within the inner tube 14 in FIG. 6. To assemble the wedge 98 into the end of the first tube 14, the tube 14 is heated and expanded. The wedge 98 is lightly tapped into position inside the tube 14. The expanded end of the tube 14 tends to contract around the end of the wedge 98, thus locking the wedge 98 in its place as shown in FIG. 6. The wedge 98 and the tube 14 are then lightly tapped into the tapered section 96 in holder 16. A small amount of adhesive can be used on the wedge 98 outside diameter before it is inserted into the tube 14, but adhesive is not necessary to lock the tube 14 in place.

Figure 8:
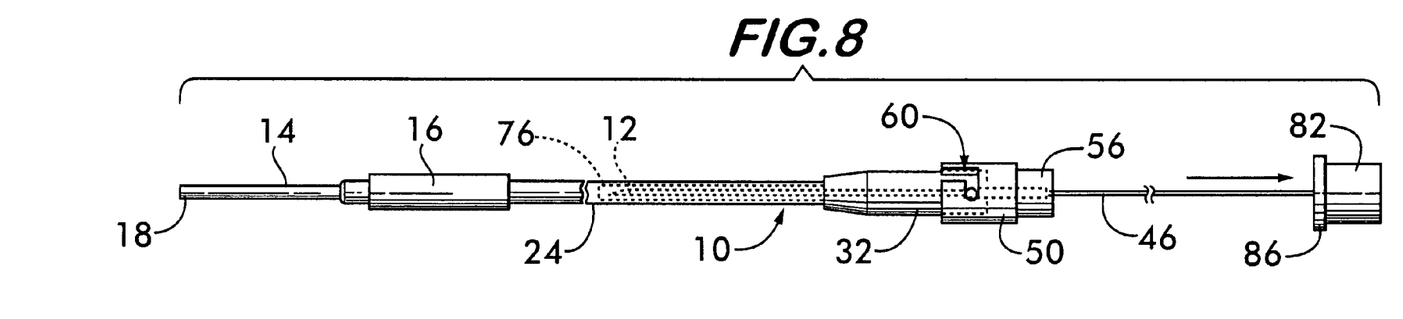
FIG. 8 is a side view of the device shown in FIG. 7 immediately after the needle has been withdrawn.

Having described the details of the safety intravenous device 10, the use of the device 10 is now described. With further reference to FIG. 7, the device 10 is shown in its initial unused form (first position) with the needle point 38 extending from the first tube 14 and the pull member 82 held by friction to the cover member bushing 56 as seen in FIGS. 2, 3 and 7. The technician using the device 10, manipulating the holder 16, inserts the needle 12 into the patient's vein to place the end 18 of the first tube 14 into the vein. Blood flows from the vein through the needle 12 and through the connector opening 48 (FIG. 5) into the outer tube 24 where the blood flash can be seen by the technician through the translucent outer tube 24. Upon seeing the blood flash, the technician knows that the needle 12 and first tube 14 are in the vein and, holding the holder 16 in place with one hand, withdraws the needle member 11, which here includes the needle 12 and the connector 44, by pulling the pull member 82 to the right with the other hand as seen in FIG. 8 (see also FIG. 4). It is seen that by pulling the pull member 82 to the right, the pull wire 46 withdraws the needle member 11 from the first tube 14, leaving the front end 18 of the tube 14 in the vein. Moreover, the pulling action pulls the needle member 11 into and through the inner tube 76 until the needle member is stopped by the elastomeric bushing 56 where the connector 44 is held by friction within the bushing recess 66 (see FIG. 3A). At this point the needle 12 is completely covered within the inner tube 76 as shown in FIG. 4, safe from accidental sticks.

Figure 9:
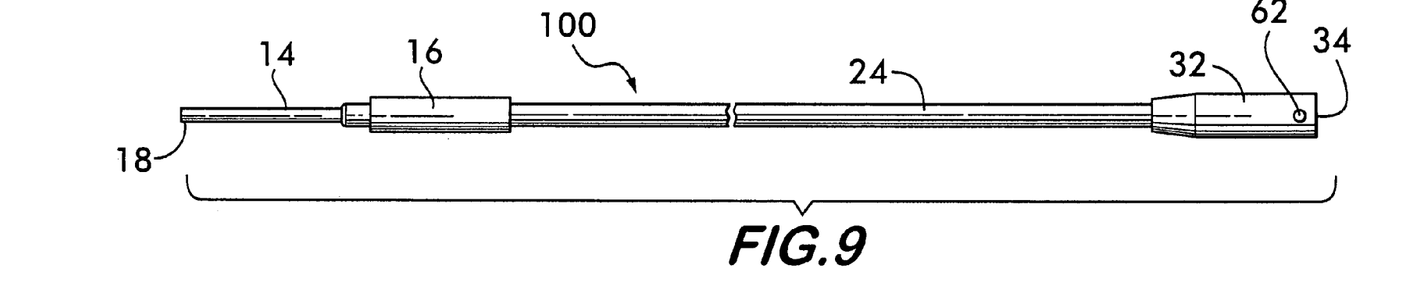
FIG. 9 is a side view after the needle assembly has been removed.

The technician then tapes the holder 16 and outer tube 24 to the patient. The cover member 50 is then removed from the receiver 32 by releasing the bayonet lock 60 (the knob 62 and slot 64), leaving the device 10 as shown in FIG. 9, a catheter assembly 100 connected to the patient, ready for connection to an intravenous supply. Put another way, a needle assembly 102, which includes the cover member 50, inner tube 76, needle member 11, pull member 82 and pull wire 46 are removed together as a unit from the catheter unit 100 (FIG. 10), and then readily disposed in a sharps container. The procedure is completed by installing a cap 104 (FIG. 2) which preferably has a complimentary elastomeric end for sealing against the opening 34 of the receiver 32, and an L slot 106, similar in configuration to the L slot 64, forming a bayonet connection with the receiver knob 62. A flexible wire 108 holds the cap 104 to the receiver 32 for ready use. Upon removal of the cap 104, the intravenous line (catheter assembly 100) is ready to receive medication.

It is seen that the embodiment of the invention overcomes several problems. It minimizes the bulk and attended cost of additional plastic parts. Furthermore, disposal of the used needle does not occur at a critical time, when the technician's attention is required for patients care and securing the first tube 14. This invention reduces costs and increases the technician's efficiency by the use of the inner tube 76 within the outer tube 24. The inner tube 76 is used as a receptacle for the used needle 12. The outer tube 24 remains in place to subsequently deliver medication. The invention provides for withdrawing the used needle 12 into the inner tube 76, but it is not removed until the technician has secured the first tube 14. Then the used needle 12, completely contained in the inner tube 76, is removed by the quick release mechanism (turning the knob 62 and by pulling the pull member 82) described above, and is discarded into the sharps container. To summarize, this invention includes the following improvements: lower costs of the device as it has lower cost and less bulky parts; lower costs to the user of the sharps container and its destruction per usage; and uninterrupted technician attention to the patient.

Although the invention has been described in language specific to the structural features shown, it is to be understood that the invention defined in the appended claims is not necessarily limited to the specific features or acts described. Rather, the specific features and acts disclosed are of a presently preferred embodiment and thus an exemplary form of implementing the claimed invention.

What is claimed is:

1. An intravenous starter device, comprising:
   a first tube having a first end, which first end includes an opening for insertion into a patient, and a second end opposite said first end;
   an outer tube in fluid communication with said first tube, said outer tube having an opening for receiving fluids to be delivered to said patient through said first tube;
   a receiver connected to and in fluid communication with said outer tube, said receiver having an opening for receiving fluids to be delivered through said outer tube;
   a needle member positioned within said first tube, said needle member comprising a needle having a sharp end extending from said first tube for insertion into said patient, and a second end opposite said sharp end;
   a cover member adjacent to and detachable from said receiver, said cover member being positioned to close said receiver opening;
   a pull member adjacent to said cover member;
   an inner tube positioned within said outer tube and connected to said cover member for movement therewith, said inner tube being sized to be slidable within said outer tube and having a needle holding section adapted to receive said needle there within; and
   a pull wire connecting said needle member to said pull member such that said needle member is moveable upon movement of said pull member from a first position wherein said sharp end of said needle extends from said first tube for entry into said patient to a second position wherein said sharp end of said needle is positioned within said inner tube.

2. A device in accordance with claim 1 wherein said inner tube is attached directly to said cover member and is sufficiently long to cover the entire needle when said needle is in said second position.

3. A device in accordance with claim 1 wherein said needle member further includes a connector attached to said needle, and wherein said pull wire is attached to said needle member via said connector, said connector having one end attached to said second end of said needle and another end attached to said pull wire.

4. A device in accordance with claim 3 wherein said connector has an opening in fluid communication with said needle to allow fluid from said needle to pass therethough, said connector opening being positioned within said outer tube.

5. A device in accordance with claim 3 wherein said pull wire extends from said pull member through an opening through said cover member and within said inner tube.

6. A device in accordance with claim 5 wherein said cover member includes a recess having one end facing said opening of said outer tube for receiving at least a portion of said needle member.

7. A device in accordance with claim 6 wherein said recess is sized so that said needle member friction fits into said recess.

8. A device in accordance with claim 1 wherein said cover member includes an elastomeric bushing having a recess for holding at least a portion of said needle member when said needle member is moved to said second position.

9. A device in accordance with claim 1 further comprising a hand grippable holder connecting said first tube to said outer tube for fluid communication therebetween.

10. A device in accordance with claim 9 wherein said holder is butterfly shaped having two flat arms extending away from one another.

11. A device in accordance with claim 1 further comprising a cap for closing said opening in said receiver after said cover member is detached from said receiver.

12. A device in accordance with claim 3 wherein said cover member includes an elastomeric bushing having a recess for holding at least a portion of said connector via friction when said needle member is moved to said second position.

13. A device in accordance with claim 9 further comprising a wedge member having an angled surface which has a diameter that increases moving away from said sharp end of said needle, and further having an opening extending therethrough, and wherein said holder has an opening therethrough which has an angled surface section that increases in diameter moving away from said sharp end of said needle, said wedge being positioned within said first tube and within said opening in said holder to lock said first tube within said holder.

14. An intravenous starter device, comprising:
   a flexible first tube having a first end for insertion into a vein and a second end opposite said first end, said first and second ends having openings through which fluid can flow;
   an outer tube in fluid communication with said second open end of said first tube, said outer tube having an opening for receiving fluids to be delivered to said vein through said first tube;
   a receiver connected to and in fluid communication with said opening of said outer tube, said receiver having an opening for receiving fluids to be delivered through said outer tube to said first tube;
   a needle member which includes a needle and a needle connector attached to said needle, said needle being positioned within said first tube and having a sharp end extending from said first tube for insertion into said patient and a second end opposite said sharp end;
   a cover member detachably connected to said receiver adjacent to said receiver opening;
   a pull member adjacent to said cover member;
   an inner tube positioned within said outer tube and having one end having an opening sized for receiving said needle member and a second end connected said inner tube being joined to said cover member for movement therewith said inner tube being moveable within said outer tube so as to be removable from said device when said cover member is detached from said receiver, said inner tube having a needle holding section for receiving within it said sharp end of said needle; and a pull wire connecting said needle member to said pull member and extending within said inner tube such that said needle member is moveable from a first position wherein said needle extends from said first tube for insertion into said patient to a second position wherein said sharp end of said needle is positioned within said inner tube after said pull member is pulled, said pull wire being attached to said needle connector.

15. A device in accordance with claim 14 wherein said connector has an opening in fluid communication with said needle to allow fluid from said needle to pass therethough.

16. A device in accordance with claim 14 wherein one of said receiver and cover member includes a slot, and the other of said receiver and said cover member includes a projection slideable within said slot, and wherein said receiver and said cover member are held together by moving said projection within said slot to a position locking the two together.

17. A device in accordance with claim 14 wherein said cover member includes an elastomeric bushing having a recess sized to frictionally hold at least a portion of said needle member, and said elastomeric bushing further has an end for compressively sealing closed said opening of said receiver.

18. An intravenous starter apparatus, comprising:
(A) a catheter assembly including:
  a first tube, said first tube having a first end which includes an opening for insertion into a patient and a second end opposite said first end;
  an outer tube in fluid communication with said first tube, said outer tube having an opening for receiving fluids to be delivered to said patient through said first tube;
  a receiver connected to and in fluid communication with said outer tube, said receiver having an opening for receiving fluids to be delivered through said outer tube; and
(B) a needle assembly removable from said catheter assembly for disposal, said needle assembly including:
  a needle member having a needle positioned within said first tube, said needle having a sharp end extending from said first tube for insertion into said patient, and a second end opposite said sharp end;
  a cover member attached to and detachable from said catheter assembly and positioned to close said receiver opening;
  a pull member detachably connected to said cover member;
  an inner tube positioned within said outer tube, said inner tube being slidable within said outer tube and having a needle holding section sized to receive at least a portion of said needle member there within, said inner tube being joined to said cover member for movement therewith so that said inner tube can be removed from said outer tube and from said catheter assembly upon detachment and movement of said cover member from said catheter assembly;
  a pull wire connecting said needle member to said pull member such that said needle member is moveable from a first position wherein said sharp end of said needle extends from said first tube to a second position wherein at least said sharp end of said needle is positioned within said inner tube after said pull member is operated to move said needle;
  wherein after being moved to said second position, said needle member is removable with said inner tube from said catheter assembly when said cover member is detached and moved from said catheter assembly.

19. A device in accordance with claim 18 wherein said inner tube has sufficient length for the entire needle to fit there within when said needle is in said second position.

20. A device in accordance with claim 19 wherein said cover member includes an elastomeric member having a recess for holding at least a portion of said needle member via friction when said needle member is moved to said second position.

* * * * *